United States Patent [19]

Rattner et al.

[11] Patent Number: 5,207,215
[45] Date of Patent: May 4, 1993

[54] ACOUSTIC PRESSURE PULSE GENERATOR

[75] Inventors: Manfred Rattner, Grossenseebach; Gerhard Buchholtz; Matthias Mahler, both of Erlangen, all of Fed. Rep. of Germany

[73] Assignee: Siemens Aktiengesellschaft, Munich, Fed. Rep. of Germany

[21] Appl. No.: 761,392

[22] Filed: Sep. 18, 1991

[30] Foreign Application Priority Data

Oct. 29, 1990 [EP] European Pat. Off. ........ 90120740.7

[51] Int. Cl.$^5$ .......................................... A61B 17/22
[52] U.S. Cl. ................................. 128/24 EL; 367/175
[58] Field of Search ............. 128/660.03, 804, 24 EL; 367/175

[56] References Cited

U.S. PATENT DOCUMENTS

| | | |
|---|---|---|
| 4,530,358 | 7/1985 | Forssmann et al. |
| 4,674,505 | 6/1987 | Pauli et al. |
| 4,697,588 | 10/1987 | Reichenberger |
| 4,715,376 | 12/1987 | Nowacki et al. ............. 128/24 EL |
| 4,840,166 | 6/1989 | Naser et al. ................. 128/24 EL |
| 4,928,672 | 5/1990 | Grasser et al. |
| 4,977,888 | 12/1990 | Rietter et al. |
| 5,031,626 | 7/1991 | Hassler et al. .............. 128/24 EL |
| 5,046,483 | 9/1991 | Ogura ......................... 128/24 EL |
| 5,095,907 | 3/1992 | Kudo et al. |

FOREIGN PATENT DOCUMENTS 3321014  10/1984  Fed. Rep. of Germany.

Primary Examiner—Ruth S. Smith
Attorney, Agent, or Firm—Hill, Steadman & Simpson

[57] ABSTRACT

An acoustic pressure pulse generator has an electrodynamic pressure pulse source formed by a membrane and a coil, so that when the membrane is electrodynamically rapidly repelled from the coil, an acoustic pressure pulse is generated in an acoustic propagation medium adjacent the membrane. A wall is disposed in the pulse generator spaced from the membrane in the direction of pressure pulse propagation, the wall preferably formed as an acoustic lens. The wall defines a space between the wall and the membrane, which is filled with acoustic propagation medium, and which is maintained liquid-tight from a second space situated at the other side of the wall, also containing an acoustic propagation medium. The acoustic propagation medium contained in the first space is maintained at a static pressure which is necessary for returning the membrane to its initial position after being repelled by the coil. The propagation medium contained in the first space can be maintained pressurized by flowing through a circulatory system which is also used for cooling that acoustic propagation medium.

14 Claims, 1 Drawing Sheet

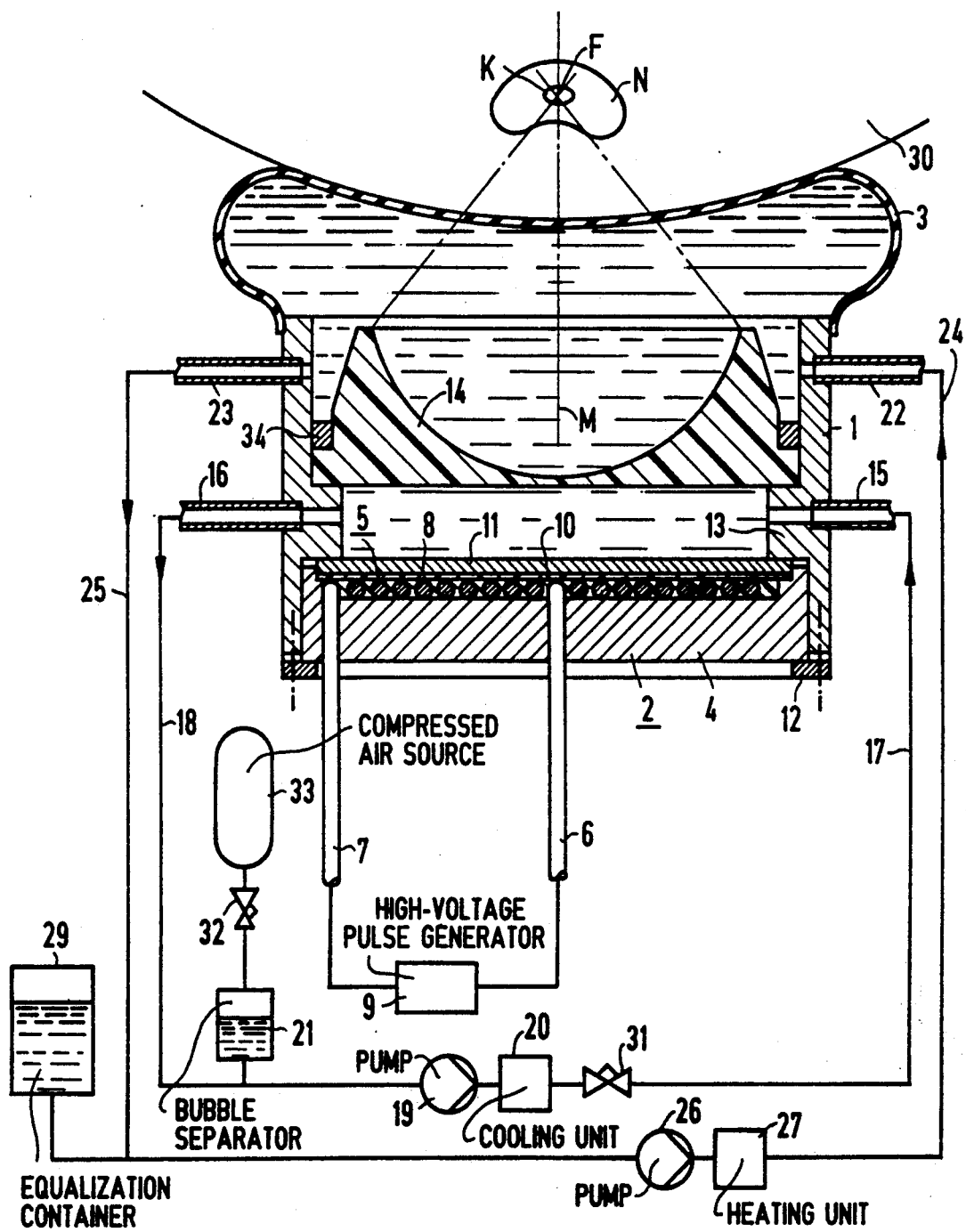

5,207,215

ACOUSTIC PRESSURE PULSE GENERATOR

BACKGROUND OF THE INVENTION

1. Field of the Invention

The present invention is directed to a pressure pulse generator, and in particular to a pressure pulse generator of the type having an electrodynamically operated coil and membrane as a pressure pulse source.

2. Description of the Prior Art

Pressure pulse generators can be used for a variety of purposes, for example in medicine to non-invasively disintegrate calculi situated in the body of a patient, or to non-invasively treat pathological tissue conditions. Positive (greater than atmospheric) pressure pulses are employed in the former case, and negative or rarefaction (less than atmospheric) pressure pulses are preferably employed in the latter case. Such pressure pulse generators can also be used for testing materials by charging specimens with pressure pulses.

A pressure pulse generator is always acoustically coupled in a suitable manner to the subject being acoustically irradiated, so that the pressure pulses generated in the acoustic propagation medium in the pressure pulse generator can be introduced into the subject. The pressure pulse generator and the subject must thus be aligned relative to each other so that the region of the subject to be acoustically irradiated is situated in the propagation path of the pressure pulses. If the pressure pulse generator generates focused shockwaves, it must also be assured that the region of the subject to be acoustically irradiated is situated in the focal region of the pressure pulses.

A pressure pulse generator of the type generally described above is disclosed in U.S. Pat. No. 4,674,505. This type of pressure pulse generator is known as an electromagnetic or electrodynamic shockwave generator, and produces positive pressure pulses using a coil arrangement. When the coil is charged with a high-voltage pulse, a magnetic field is generated extremely quickly. This magnetic field induces a current in a membrane disposed opposite the coil arrangement. The membrane contains conductive material, and current is thus caused to flow in the membrane in a direction opposite to the current flowing through the coil. A magnetic field opposite in direction to the magnetic field associated with the coil arrangement is thus generated in the membrane. This causes the membrane to be rapidly repelled from the coil arrangement as a consequence of the magnetic repulsion forces. A pressure pulse is thereby introduced into an acoustic propagation medium adjacent the membrane, and gradually intensifies to form a shockwave along its propagation path.

Such shockwave generators have a relatively low efficiency, so that a large part of the electrical input energy is converted into heat. This results in the pressure pulse source gradually heating during use. Because elevated operating temperatures of the pressure pulse source can result in a premature failure thereof, particularly due to a failure of the membrane as a result of high mechanical stresses, it is provided in a pressure pulse generator disclosed in European Application 0 265 741 that the acoustic propagation medium be conducted through a circulating cooling system during operation. This makes it possible to eliminate the heat emitted by the pressure pulse source which is contained in the acoustic propagation medium. In the case of this known pressure pulse generator, however, the cooling effect is not sufficient under all circumstances. In this known pressure pulse generator, "heat pockets" can form for which a sufficient heat elimination is not guaranteed.

Another problem associated with pressure pulse sources of the type described above is that the membrane must be returned to its initial position after the production of a pressure pulse. Only in this way is it insured that the membrane will have a defined initial position, in which it is pressed against the coil arrangement, before a shockwave is generated. This is a prerequisite for insuring that the acoustic characteristics of successively generated shockwaves coincide with adequate precision. In a pressure pulse generator disclosed in European Application 0 188 750, the return of the membrane to its initial position is accomplished by charging that side of the membrane facing away from the acoustic propagation medium with negative pressure. Although this insures a reliable return of the membrane to its initial position, a substantial design outlay is required, and a negative pressure source must be provided.

A pressure pulse generator is disclosed in German OS 33 12 014 wherein the membrane is returned to its initial position by a pressurized propagation medium.

SUMMARY OF THE INVENTION

It is an object of the present invention to provide an electrodynamic pressure pulse generator wherein a premature failure of the pressure pulse generator as a consequence of inadequate cooling is avoided, and wherein the generation of successive pressure pulses having substantially coinciding acoustic characteristics is insured, in an economic and structurally simple manner.

The above object is achieved in accordance with the principles of the present invention in a pressure pulse generator having a pressure pulse source in the form of a membrane which is displaced by a coil for generating acoustic pressure pulses in an acoustic propagation medium, and having a wall disposed spaced from the membrane which defines, with the membrane, a first space which contains a liquid acoustic propagation medium. The first space is maintained liquid-tight by the wall from a second space situated on the other side of the wall, which also contains an acoustic propagation medium. The acoustic propagation medium contained in the first space is pressurized at a static pressure which is greater than the ambient pressure so that the membrane is returned to its initial position after displacement of the membrane. The acoustic propagation medium in the first space is also caused to flow through a cooling means.

Because the acoustic propagation medium flowing through a cooling means is situated in the first space limited by the membrane and by the wall, good flow conditions are present for the acoustic propagation medium, so that no heat pockets can form and a good cooling effect is thus assured. Because the acoustic propagation medium is maintained under a pressure which is greater than the ambient pressure, the membrane is also returned to its initial position after the generation of a pressure pulse, so that the measures required in conventional devices for charging the side of the membrane facing the coil with negative pressure can be eliminated. Dependent on the stiffness of the membrane, moreover, only a slight elevated pressure may be needed, such as on the order of magnitude of less than one bar, to reliably insure return of the membrane. The pressure which is already required for maintaining the flow of the acoustic propagation medium through the cooling means will usually be sufficient to also function to return the membrane to its initial position.

The pressure pulse generator disclosed herein has the additional advantage that, due to the elevated pressure prevailing in the first space, the risk of harmful cavitation phenomena is significantly diminished, and cavitation bubbles which may nonetheless arise are quickly eliminated from the first space as a consequence of the flow of the acoustic propagation medium.

The wall is preferably fashioned of a material having a low acoustic damping, and has an acoustic impedance matched to that of the acoustic propagation media situated in the first and second spaces.

The static pressure of the acoustic propagation medium contained in the first space, or the quantity of acoustic propagation medium flowing through the cooling means per time unit, may be adjustable. This provides the possibility of adapting the restoring force acting on the membrane, or the cooling action, to the prevailing operating conditions.

The acoustic propagation medium flows through the cooling means in a closed circulation loop. This makes it possible to easily degassify the acoustic propagation medium and to provide it, for example, with corrosion-inhibiting additives.

An especially good cooling action is achieved if the acoustic propagation medium in the first space is caused to flow in a direction which is substantially parallel to the surface of the membrane.

In the preferred embodiment of the invention, the wall separating the first space from the second space is shaped as an acoustic lens. This is advantageous particularly if the pressure pulses emanating from the membrane require focusing, and thus an acoustic lens must be present in any event.

The second space can be terminated by a flexible coupling membrane, and can be in communication with an equalization container or reservoir. This makes it possible to easily deform the coupling membrane, which serves the purpose of acoustically coupling the pressure pulse generator to a subject to be acoustically irradiated, i.e., to deform the coupling membrane in the manner required for the particular alignment of the pressure pulse generator relative to the subject. Because the first space and the second space are separated from each other by the wall (which may be in the form of the acoustic lens) and only the acoustic propagation medium separated in the first space flows through the cooling means, it is possible to match the temperature of the acoustic propagation medium situated in the second space to that of the subject to be acoustically irradiated. This can be particularly useful for increasing the comfort of a human patient, without having a disadvantageous influence on the desired cooling effect, since the acoustic propagation medium situated in the first space will normally be at a much lower temperature.

DESCRIPTION OF THE DRAWING

The single drawing is a side sectional view of a pressure pulse source constructed in accordance with the principles of the present invention, with associated operating components being schematically shown.

DESCRIPTION OF THE PREFERRED EMBODIMENTS

A pressure pulse generator constructed in accordance with the principles of the present invention is shown in an exemplary embodiment in the drawing in the form of a shockwave generator for disintegrating calculi in the body of a patient (lithotripsy apparatus). This shockwave generator includes a tubular housing 1 having one end terminated by a shockwave source, generally referenced 2, and having an opposite end terminated by a flexible coupling membrane 3.

The shockwave source 2 is formed by a coil 5 disposed on a planar seating surface of a coil carrier 4. The coil 5 has terminals 6 and 7, with spiral turns therebetween, one of the turns being referenced 8. The coil carrier is formed of an electrically insulating material, for example aluminum oxide ceramic. The space between the turns 8 of the coil 5 is filled with an electrically insulating casting resin. The terminals 6 and 7 of the coil 5 are connected to a high-voltage pulse generator 9.

The side of the coil 5 facing away from the coil carrier 4 is covered with an insulating foil 10, to which a planar membrane 11, such as a circular disk, is adjacent. The membrane 11 is composed of, or contains, electrically conductive material, for example copper. The membrane 11, the insulating foil 10 and the coil 5 are combined with the coil carrier 4 by means of a centering flange to form a single unit. This unit is pressed against a shoulder 13 provided in a bore of the housing 1 by a ring 12. The ring 12 is pressed against the coil carrier 4 by several screws, the center lines of two such screws being schematically indicated. Suitable sealants (not shown) are employed so that the membrane 11 presses liquid-tight against the shoulder 13.

A plano-concave acoustic lens 14 consisting of, for example, polystyrol, has a planar side which presses liquid-tight against that side of the shoulder 13 facing away from the membrane 11. The positive lens 14 is axially fixed by a retainer ring 34 (schematically indicated) which is introduced into the bore of the housing 1. A liquid, for example water, is situated in a first space which is limited between the positive lens 14 and the membrane 11 (surrounded by the housing 1). The first space has an inlet 15 and an outlet 16, to which an inlet line 17 and an outlet line 18 are respectively connected. Water can thus be circulated through this first space by means of a pump 19, and is conducted through a cooling unit 20. A bubble separator 21, wherein gas bubbles which may possibly arise can collect, is also connected to the outlet line 18. The pump 19 and the cooling unit 20 are followed by a suitable regulating valve 31, which allows the quantity of water flowing through the first space, and thus through the cooling unit 20, per time unit to be set. The bubble separator 21 is connected by means of a suitable regulating value 32 to a compressed air source 33, so that it is possible to set the static pressure prevailing in the first space by means of the regulating valve 32.

A liquid, for example water, is also contained in a second space, situated between the positive lens 14 and the coupling membrane 3, the second space being separated liquid-tight from the first space by the positive lens 14. The second space also has an inlet 22 and a discharge 23, respectively connected to an inlet line 24 and an outlet line 25. Water, as the acoustic propagation medium in the second space, is conducted through a heating unit 27 by a pump 26. The heating unit 27 raises the temperature of the water in the second space to, for instance, the body temperature of a patient 30 to be treated. An equalization (or balancing, or compensation) container or reservoir 29 is connected to the outlet line 25. This container 29 accepts the quantity of water which has been displaced from the second space when the shockwave generator is pressed against the body of the patient 30. The equalization container 29 simultaneously serves as a bubble separator.

Shockwaves are generated in a known manner with the above-described shockwave generator by charging the coil 5 with a high-voltage pulse from the high-voltage pulse generator 9. In response thereto, the coil 5 generates a magnetic field extremely quickly, which induces a current in the membrane 11 in a direction opposite to the direction of the current flowing through the coil 5. The current in the membrane 11 is also associated with a magnetic field, which has a direction opposite to the direction of the magnetic field associated with the current in the coil 5. As a consequence of the repulsion forces which arise, the membrane 11 is suddenly and rapidly moved away from the coil 5, so that a pressure pulse, which is initially planar, is introduced into the water serving as the acoustic propagation medium situated in the first space adjacent the membrane 11. This pressure pulse is focused to a focal zone F by the positive lens 14, in the manner indicated by the dashed lines in the drawing. The focal zone F is disposed on a center axis M of the shockwave generator.

The focused pressure pulse propagates in the water contained in the second space as the acoustic propagation medium. By using a suitable locating system, such as an x-ray system, the shockwave generator can be pressed against the body of the patient 30 by means of the coupling membrane 3 in a position so that a calculus K to be disintegrated, for example a stone contained in a kidney N is situated in the focal zone F. The calculus K can be disintegrated by a series of pressure pulses into fragments which are so small that they can be eliminated naturally. The pressure pulses emanating from the membrane 11 gradually intensify along their path through the acoustic propagation media in the first and second spaces, as well as in the body tissue of the patient 30, to form shockwaves, which are pressure pulses having an extremely steep leading front.

As a consequence of the circulation of the water in the first space through the cooling unit 20 in the manner described above, it is assured that the dissipated heat arising during operation of the pressure pulse generator can be eliminated without problems. The obtainable cooling effect is enhanced if the flow direction of the acoustic propagation medium in the first space proceeds approximately parallel to the surface of the membrane 11. This is insured due to the placement of the inlet 15 and the outlet 16 opposite each other, which prevents the formation of heat pockets. The cooling effect is further promoted by circulating through the cooling unit 20 only the water which is situated immediately in the region of the membrane 11. This is achieved by the acoustic lens 14 acting as a partition between the first space, adjacent the membrane, and the second space situated between the positive lens 14 and the coupling membrane 3. The cooling effect can be adapted to individual requirements by operation of the regulating valve 31, the cooling effect being greater as the valve 31 is opened. Moreover, the cooling unit 20 can be adjustable in a known manner to have a greater or lesser cooling effect.

The water situated in the first space is pressurized at a static positive pressure of, for example, one bar compared to ambient pressure. As a result, the membrane 11, whose thickness is shown exaggerated in the drawing, is returned to its initial position after a pressure pulse (or a shockwave) has been produced so that the membrane 11 lies flush against the surface of the coil 5, with the insulating foil 10 interposed therebetween. This insures that successively generated shockwaves will have the same acoustic characteristics. The static pressure of the water situated in the first space can be adapted to individual requirements by actuating the regulating valve 32. The water in the first space circulating through the cooling unit 20 will have, for example, a temperature below room temperature when it enters into the first space. Since this water is separated from the water (acoustic propagation medium) in the second space, adjacent the body of the patient 30 with the coupling membrane 3 therebetween, the water in the second space can be heated by the heating unit 27 to a temperature which is comfortable for the patient 30, for example body temperature, without significantly diminishing the obtainable cooling effect in the region of the pressure pulse source 2.

A feedback system (not shown) can be provided so that the cooling effect of the cooling unit 20 and/or the flow rate of water through the regulating valve 31 is/are regulated so that the water flows into the first space with a preselectable, constant temperature. Similarly, a feedback system (not shown) can be employed so that the static pressure prevailing in the first space can be regulated dependent on the amplitude of the generated pressure pulses. The amplitude of the pressure pulses increases with increasing amplitude of the high-voltage pulses supplied to the coil 5, and the static pressure increases with increasing amplitude of the pressure pulses.

In the exemplary embodiment described above, the same acoustic propagation medium, namely water, is present in the first and second spaces. This is not necessary, and it is possible to use different propagation media in the two spaces.

Although the invention has been described above in the context of the example of a shockwave generator for medical use, the inventive concept disclosed herein can be used in other types of pressure pulse generators.

Although modifications and changes may be suggested by those skilled in the art, it is the intention of the inventors to embody within the patent warranted hereon all changes and modifications as reasonably and property come within the scope of their contribution to the art.

We claim as our invention:
1. A pressure pulse generator comprising:
a housing;
electrodynamic means, including a membrane, for generating acoustic pressure pulses by rapid displacement of said membrane in a first liquid acoustic propagation medium disposed adjacent said membrane;
a rigid wall in said housing spaced from said membrane and defining with said membrane and said housing a first non-expandable space in which said first liquid acoustic propagation medium is contained;

a second acoustic propagation medium contained in a second space on an opposite side of said wall and said wall maintaining said first and second acoustic propagation media separated;

means for cooling said first liquid acoustic propagation medium disposed outside of said first space; and means in fluid communication with said first space for circulating and pressurizing said first liquid acoustic propagation medium at a static pressure for returning said membrane to an initial position after generation of an acoustic pressure pulse, and for simultaneously conducting said first liquid acoustic propagation medium through said means for cooling said first liquid acoustic propagation medium.

2. A pressure pulse generator as claimed in claim 1 further comprising means for adjusting said static pressure of said first liquid acoustic propagation medium in said first space.

3. A pressure pulse generator as claimed in claim 1 wherein said means for circulating and pressurizing is a closed circulation loop including means for conducting said first liquid acoustic propagation medium through said loop at a flow rate and including said means for cooling.

4. A pressure pulse generator as claimed in claim 3 further comprising means for adjusting said flow rate of said first liquid acoustic propagation medium through said loop.

5. A pressure pulse generator as claimed in claim 1 further comprising means for maintaining a flow of said first liquid acoustic propagation medium in said first space in a direction substantially parallel to a surface of said membrane.

6. A pressure pulse generator as claimed in claim 1 wherein said wall is an acoustic lens.

7. A pressure pulse generator as claimed in claim 1 wherein said second acoustic propagation medium is a liquid, and further comprising:

a flexible coupling membrane closing one end of said second space, and further comprising an equalization container in fluid communication with said second space for receiving said second liquid acoustic propagation medium if said flexible coupling membrane is inwardly deformed.

8. A pressure pulse generator comprising:

a housing;

electrodynamic means, including a membrane, disposed at a first end of said housing for generating acoustic pressure pulses by rapid displacement of said membrane in a first liquid acoustic propagation medium disposed adjacent said membrane;

a flexible coupling membrane closing an opposite end of said housing;

a rigid wall in said housing spaced from said membrane and from said flexible coupling membrane and defining a first non-expandable space in said housing between said membrane and said wall and a second space in said housing between said flexible coupling membrane and said wall, said first and second spaces being liquid-tight relative to each other;

said first liquid acoustic propagation medium contained in said first space and a second liquid acoustic propagation medium contained in said second space;

means for cooling said first liquid acoustic propagation medium disposed outside of said first space; and means in fluid communication with said first space for circulating and pressurizing said first liquid acoustic propagation medium at a static pressure for returning said membrane to an initial position after generation of an acoustic pressure pulse, and for simultaneously conducting said first liquid acoustic propagation medium through said means for cooling said first liquid acoustic propagation medium.

9. A pressure pulse generator as claimed in claim 8 further comprising means for adjusting said static pressure of said first liquid acoustic propagation medium in said first space.

10. A pressure pulse generator as claimed in claim 8 wherein said means for circulating and pressurizing is a closed circulation loop including means for conducting said first liquid acoustic propagation medium through said loop at a flow rate and including said means for cooling.

11. A pressure pulse generator as claimed in claim 10 further comprising means for adjusting said flow rate of said first liquid acoustic propagation medium through said loop.

12. A pressure pulse generator as claimed in claim 8 further comprising means for maintaining a flow of said first liquid acoustic propagation medium in said first space in a direction substantially parallel to a surface of said membrane.

13. A pressure pulse generator as claimed in claim 8 wherein said wall is an acoustic lens.

14. A pressure pulse generator as claimed in claim 8 further comprising:

an equalization container in fluid communication with said second space for receiving said second liquid acoustic propagation medium if said flexible coupling membrane is inwardly deformed.

* * * * *